US00PP16215P2

(12) United States Plant Patent
Zaias

(10) Patent No.: US PP16,215 P2
(45) Date of Patent: Jan. 24, 2006

(54) *LIRIOPE* PLANT NAMED 'CASSIDY'

(50) Latin Name: *Liriope spicata*
Varietal Denomination: Cassidy

(75) Inventor: Nardo Zaias, Miami Beach, FL (US)

(73) Assignee: Magaly Zaias Fast, Coral Springs, FL (US)

( * ) Notice: Subject to any disclaimer, the term of this patent is extended or adjusted under 35 U.S.C. 154(b) by 88 days.

(21) Appl. No.: 10/973,787

(22) Filed: Oct. 26, 2004

(30) Foreign Application Priority Data

Nov. 6, 2003 (QZ) ..... PBR 20032043

(51) Int. Cl.
*A01H 5/00* (2006.01)

(52) U.S. Cl. ..... Plt./373

(58) Field of Classification Search ..... Plt./373, Plt./263

See application file for complete search history.

*Primary Examiner*—Anne Marie Grunberg
*Assistant Examiner*—June Hwu
(74) *Attorney, Agent, or Firm*—Mark P. Bourgeois

(57) ABSTRACT

A new cultivar of *Liriope* plant named 'Cassidy' that is characterized by a compact habit and linear, curly green leaves.

1 Drawing Sheet

Botanical classification: *Liriope spicata.*
Variety denomination: 'Cassidy'.

BACKGROUND OF THE INVENTION

The present invention relates to a new and distinct cultivar of *Liriope* plant botanically known as *Liriope spicata* and hereinafter referred to by the cultivar name 'Cassidy'.

The new cultivar was discovered in 1996 by the inventor in a cultivated area of Puerto Rico. 'Cassidy' was discovered as a naturally occurring whole plant mutation of an unnamed *Liriope spicata* (not patented).

Asexual reproduction by tissue culture of the new cultivar 'Cassidy' was first performed in 1998 in Puerto Rico.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Liriope* cultivar 'Cassidy'. These traits in combination distinguish 'Cassidy' as a new and distinct cultivar.

1. *Liriope* 'Cassidy' exhibits a compact habit.
2. *Liriope* 'Cassidy' exhibits linear, curly leaves.
3. *Liriope* 'Cassidy' exhibits green leaves.

The new cultivar 'Cassidy' is distinguishable from the parent *Liriope spicata*, by the following characteristics:

1. 'Cassidy' has curly leaves. The leaves of the parent plant are not curly.
2. 'Cassidy' has a more compact habit. The parent plant has exhibits more spreading.

The new cultivar 'Cassidy' can be distinguished from the *Liriope spicata* cultivar 'Silver Dragon', by the following characteristics:

1. 'Cassidy' has curly leaves. The leaves of 'Silver Dragon' are not curly.

2. 'Cassidy' has green leaves. The leaves of 'Silver Dragon' are variegated green and white.

BRIEF DESCRIPTION OF THE DRAWING

The accompanying photograph illustrates the distinguishing traits of *Liriope* 'Cassidy'. The plant in the photograph shows an overall view of a 2 year old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Liriope* cultivar named 'Cassidy'. Data was collected in Evergem, Belgium. The plants were 2 year old glass greenhouse grown plants in 11 cm. diameter containers. The temperature ranged from 21 to 25° Centigrade. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Cassidy' has not been tested under all possible conditions and phenotypic differences may be observed with variations in environmental, climatic, and cultural conditions, however, without any variance in genotype.

Botanical classification: *Liriope spicata* 'Cassidy'.
Parentage: 'Cassidy' is a naturally occurring whole plant mutation of an unnamed *Liriope spicata.*
Annual or perennial: Perennial.
Use: Ornamental.
Vigor: Moderate.
Growth habit: Broad spreading, leaves grow from basal clumps.
Plant shape: Flattened globose.
Suitable container size: 12 cm container.

Height: Average 20 cm. in height.
Width: Average 38 cm. in width.
Hardiness: USDA Zone 10.
Growth rate: Approximately 5 cm. per month.
Propagation: Tissue Culture.
Time to initiate roots in winter: Approximately 35 days to produce roots on an initial cutting.
Time to initiate roots in summer: Approximately 28 days to produce roots on an initial cutting.
Crop time: Approximately 9 months to produce a finished plant from a rooted cutting.
Root system: Fine and fibrous.
Root color: 168D.
Stem: Leaves grow from basal clumps, Average number of clumps: 3.
Foliage:

*Texture.*—Smooth, glossy, slightly leatherly.
*Leaf arrangement.*—Alternate.
*Compound or single.*—Single.
*Quantity of leaves per clump.*—Average 28.
*Leaf shape.*—Linear, strongly curved.
*Leaf apex.*—Long acuminate.
*Leaf length.*—Average 38.3 cm. in length.
*Leaf width.*—Average 7.0 mm. in width.
*Pubescence.*—Absent.
*Leaf margin.*—Entire.
*Vein pattern.*—Parallel.
*Young leaf color* (*lower surface*).—143A with the base varying from 145C to 154D.
*Young leaf color* (*upper surface*).—143A with the base varying from 145C to 154D.
*Mature leaf color* (*lower surface*).—137A with a base 145D.
*Mature leaf color* (*upper surface*).—Varies between 139A and 147A with a base 145A to 145B.
*Vein color upper surface.*—137A, 145D at base.
*Vein color lower surface.*—139A.
*Leaf attachment.*—Sessile.
*Durability of foliage to stress.*—High.
*Leaf wings*—At the base of each leaf is a pair of wings, 4.5 cm. in length and 4 mm. in width, color 164D both sides.

Flower: Flowering has not been observed.
Disease and pest resistance: 'Cassidy' has not been observed for disease or pest resistance.

It is claimed:

1. A new and distinct variety of *Liriope* plant named 'Cassidy' as described and illustrated.

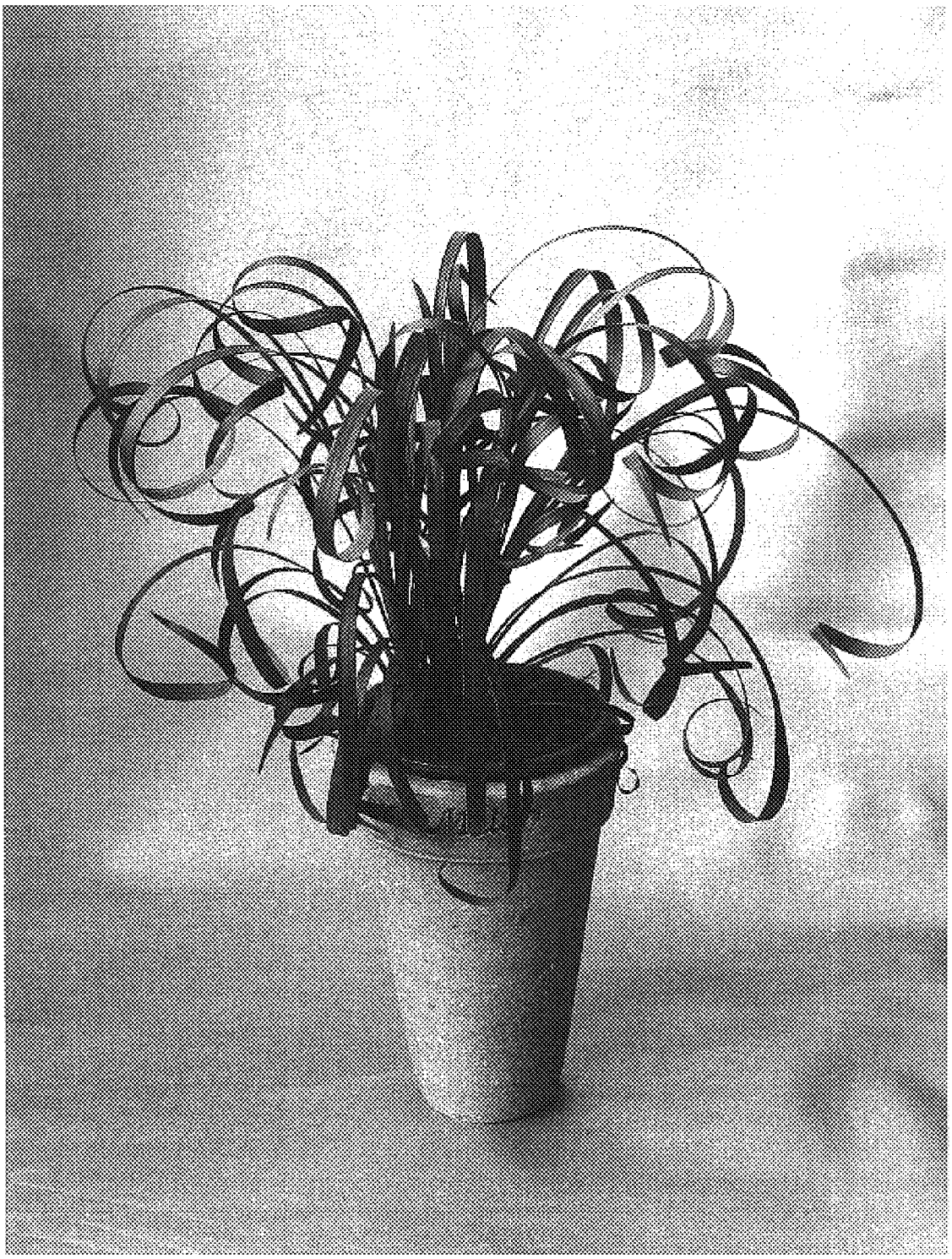

* * * * *